(12) United States Patent
Goodman

(10) Patent No.: US 9,561,111 B1
(45) Date of Patent: Feb. 7, 2017

(54) SHOULDER JOINT IMPLANT

(76) Inventor: Floyd G. Goodman, Williamston, MI (US)

( * ) Notice: Subject to any disclaimer, the term of this patent is extended or adjusted under 35 U.S.C. 154(b) by 0 days.

(21) Appl. No.: 13/068,119

(22) Filed: May 3, 2011

Related U.S. Application Data

(60) Provisional application No. 61/343,783, filed on May 4, 2010, provisional application No. 61/395,686, filed on May 14, 2010, provisional application No. 61/402,120, filed on Aug. 24, 2010.

(51) Int. Cl.
*A61F 2/40* (2006.01)
(52) U.S. Cl.
CPC ............................ *A61F 2/40* (2013.01)
(58) Field of Classification Search
CPC ........ A61F 2/40; A61F 2/4003; A61F 2/4014; A61F 2/4036; A61F 2/4081
USPC .......................................... 623/19.11–19.14
See application file for complete search history.

(56) References Cited

U.S. PATENT DOCUMENTS

| 4,550,450 | A | 11/1985 | Kinnett |
| 6,248,132 | B1* | 6/2001 | Harris ................... 623/22.15 |
| 7,959,680 | B2 | 6/2011 | Stone et al. |
| 2004/0039449 | A1* | 2/2004 | Tornier .................. 623/19.13 |
| 2006/0079963 | A1 | 4/2006 | Hansen |
| 2007/0179624 | A1* | 8/2007 | Stone et al. ............ 623/19.13 |

OTHER PUBLICATIONS

Murphy et al., "Acromion-fixation of glenoid components in total shoulder arthroplasty," J. Biomechanics 38 (2005) 1702-1711.

* cited by examiner

*Primary Examiner* — Brian Dukert
(74) *Attorney, Agent, or Firm* — Christopher John Rudy

(57) ABSTRACT

Captured element shoulder joint implant may be configured with a captured humeral ball; in a reverse shoulder configuration; to have a barrel- or disc-like humeral head to recessed glenoid articulation; and so forth. Multi-point fixation glenoid component may be provided. A humeral implant may have a universal joint connection, which can be mounted to or in a humeral bone and provide for a center of movement generally within a volume defined by an upper head of a normal humerus.

15 Claims, 11 Drawing Sheets

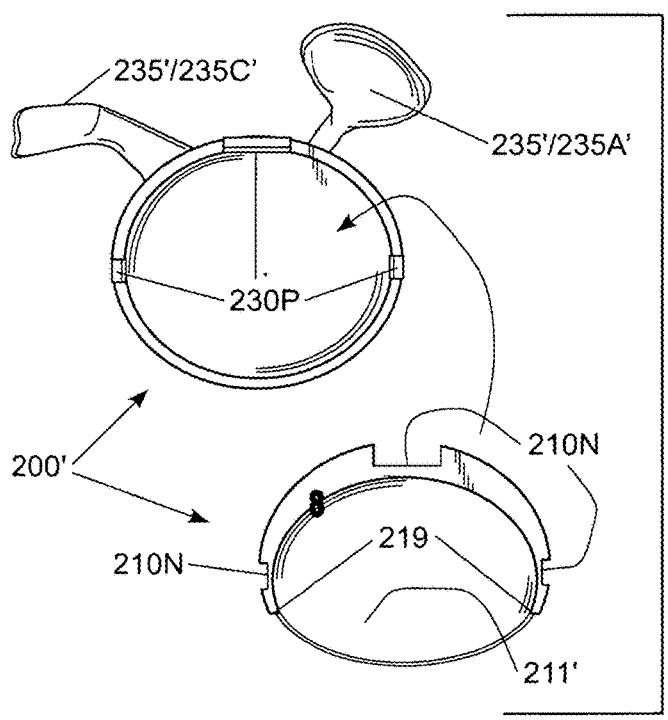
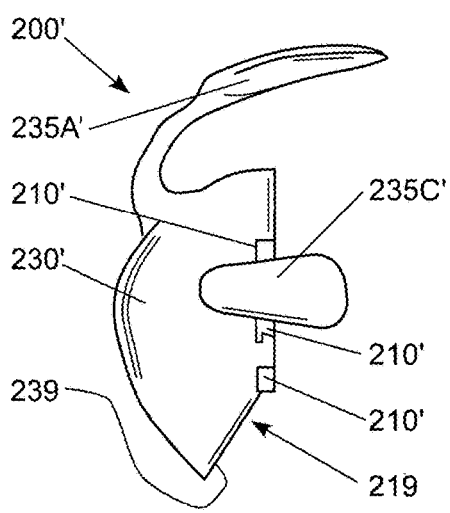
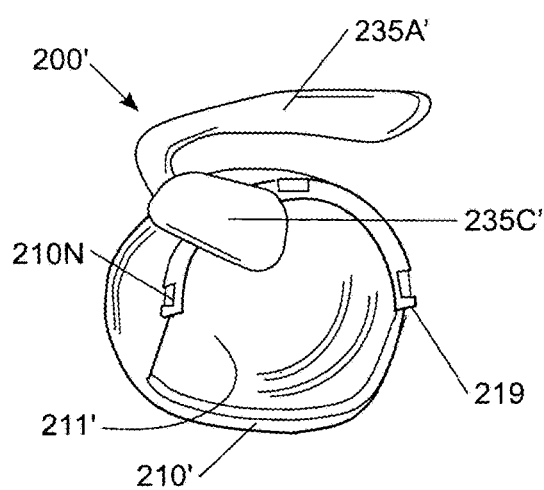
Fig. 12
Fig. 13
Fig. 14

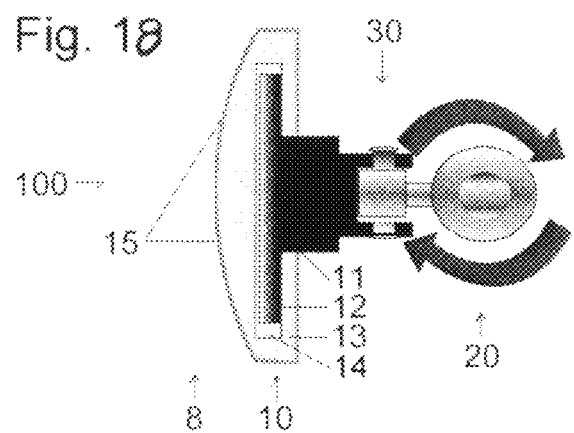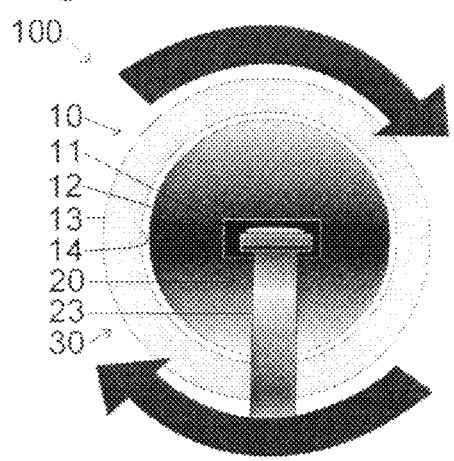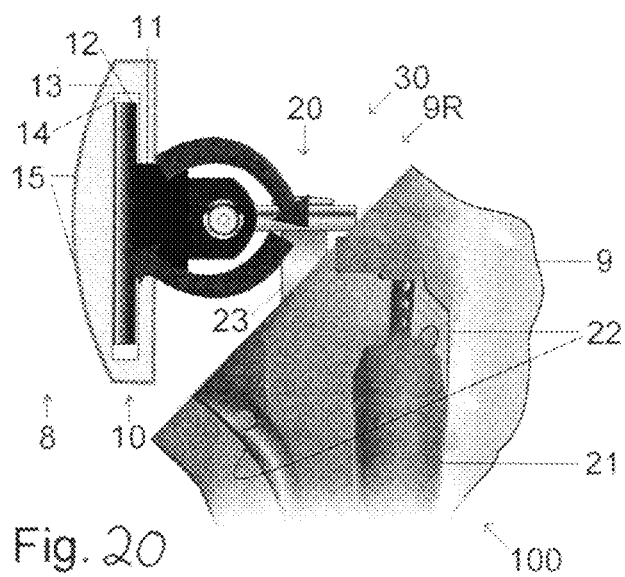

SHOULDER JOINT IMPLANT

This claims benefits under 35 USC 119(e) of U.S. provisional patent application No. 61/343,783 filed on May 4, 2010 A.D., 61/395,686 filed on May 14, 2010 A.D., and 61/402,120 filed on Aug. 24, 2010 A. D. The specifications of those applications, of course to include their drawings, are incorporated herein by reference in their entireties.

FIELD OF THE INVENTION

This concerns a joint implant or component for the glenohumeral joint.

BACKGROUND TO THE INVENTION

Various shoulder joint implant art is known. Such an implant can be an ensemble for total or perhaps partial joint replacement of the main joint of the shoulder, the glenohumeral joint, the configuration of which, conventionally, attempts to mimic the configuration of the natural glenohumeral joint, generally having an implanted artificial humeral component with a ball-like head, say, of metal or ceramic, which articulates in and against a generally shallow open cup, say, of polyethylene or metal, of an implanted artificial glenoid component in a total arthroplasty or perhaps against the natural glenoid cup in a hemiarthroplasty. As good as such art can be, it is not without its drawbacks. Among these are that natural range of motion is difficult if not well nigh impossible to achieve, and the shoulder, being an enarthrodial joint and the joint of the body with the greatest range of motion by way of having its head held in place to a great extent by means of muscle, fibrous capsule and ligamentous tendon structures in a shallow cup, the "glenoid," can be prone to dislocation, even after joint replacement surgery with a device of such art. The most frequent cause of unsuccessful shoulder joint replacement is failure of fixation through loosening of known glenoid components, not infrequently caused by compromise of mounting of a metal shell holding the cup, or compromise of a cemented plastic cup, to a surgically prepared portion on the quite thin and fragile scapular bone (glenoid area). This deficit of glenoid area supporting bone may need to be addressed.

Reverse shoulder implants are also known. In such implants, a ball head is provided as part of the glenoid component, with a corresponding cup as part of the humeral component. Such art, too, is not without its drawbacks, among which may include dislocation and/or glenoid component loosening as with the more anatomically conventional shoulder joint implants discussed in general above.

It would be desirable to improve upon the art. It would be desirable, in particular, to provide a shoulder joint implant that ameliorates if not solves in general one or more of the problems in the art, notably dislocation, loosening and/or supporting bone deficit of the glenoid area, and motion range. It is desirable to provide alternative(s).

A FULL DISCLOSURE OF THE INVENTION

In one embodiment is provided, in general, a shoulder joint implant or implant component with or for a captured ball coupling mechanism comprising at least one of an artificial humeral component and an artificial glenoid component, which is useful in or as an ensemble for total joint replacement of a glenohumeral joint, wherein:
the humeral component embraces a ball-like head attachable to a universal joint connection, which can be mounted to or in a humeral bone; and
the glenoid component embraces a closable glenoid cup having a concave articular surface, which glenoid component can envelope and surround the ball-like head of the humeral component when the humeral component is mounted to the glenoid component, such that the head can articulate against the articular surface of the glenoid cup and such that the universal joint connection is outside the glenoid component.

Provided generally hereby also is a glenoid component for a glenohumeral joint implant comprising a body of a cup, or a mount for a glenoid cup to be held with the mount, which provides multi-point fixation and includes at least one elongate mounting arm for attaching to spaced-apart portion(s) of bone of a shoulder such as a scapular bone, for example, the coracoid and acromion.

In another embodiment is provided, in general, a shoulder joint implant or implant component with or for a captured part coupling mechanism comprising at least one of an artificial humeral component and an artificial glenoid component, which is useful in or as an ensemble for total joint replacement of a glenohumeral joint, wherein:
the humeral component embraces an articulatable part attachable to a universal joint connection, which can be mounted to or in a humeral bone; and
the glenoid component embraces a closable glenoid part having a corresponding articular surface to that of the articulatable part, which glenoid component can envelope and surround the articulatable part of the humeral component when the humeral component is mounted to the glenoid component, such that the articulatable part can articulate against the corresponding articular surface of the glenoid part and such that the universal joint connection is outside the glenoid component.

Provided generally hereby also is a glenoid component for a glenohumeral joint implant comprising a body of an articulatable part, or a mount for an articulatable glenoid part to be held with the mount, which provides multi-point fixation and includes at least one elongate mounting arm for attaching to spaced-apart portion(s) of bone of a shoulder such as a scapular bone, for example, the coracoid and acromion.

In yet another embodiment is provided, in general, a shoulder joint implant or implant component for the glenohumeral joint, which comprises an artificial humeral component, which is useful in or as an ensemble for total joint replacement arthroplasty of a glenohumeral joint or which is useful in hemiarthroplasty in a glenohumeral joint where the artificial humeral component articulates against a natural glenoid, wherein:
the humeral component embraces a radial head for registering against an artificial glenoid cup or natural glenoid tissue, and articulating against the same upon surgical implantation, which humeral component is attachable to a universal joint connection, which can be mounted to or in a humeral bone and provide for a center of movement; and
the center of movement is generally within a volume defined by an upper head of a normal humerus, which otherwise would be resected and absent when the humeral component is implanted, and generally centered therein.

The invention is useful in connection with orthopedic repair of the shoulder.

Significantly, by the invention, not only is an alternative provided the art, but the art is advanced in kind, and one or more of its problems is ameliorated if not solved in general. Notably, the propensity for if not occurrence of dislocation can be reduced if not nearly or even completely eliminated, even in cases where viable rotator cuff structures are compromised or absent. Additionally, for example, reverse shoulder configurations are provided where the humeral component has a cup configuration as an articulatable part and the glenoid component has a ball as the corresponding articular surface. Then, too—versus known glenoid components, which are typically attached to the prepared glenoid area by single point fixation of their glenoid cup or shell for a cup insert such as through bony ingrowth to a porous coating, surgical cement and/or several screws to the bone— with the present invention, loosening of the glenoid component can be reduced if not nearly or even completely eliminated through multi-point fixation. Furthermore, enhanced stability of the glenoid component is provided through the multi-point fixation. Thus, supporting bone deficit of the glenoid area is more comprehensively addressed. Range of motion can be maintained after implantation at high levels. Yet additionally, a most natural motion and range of motion can be imparted to the shoulder of the human patient after surgical implantation of the implant, to include by restoration of the center of rotation as in a normal shoulder. Owing to the configuration of the humeral component with restoration of the center of rotation as in a normal shoulder, the propensity for if not occurrence of dislocation can be further reduced; additionally improved stability in a rotator cuff deficient shoulder is provided; and so too is further help in preventing or lessening loosening of an accompanying glenoid prosthetic component. Implantation of the device can be successfully carried out by a wide range of nearly all orthopedic surgeons, not just the most skilled. Numerous further advantages attend the invention.

The drawings form part of the specification hereof. With respect to the drawings, which are not necessarily drawn to scale, the following is briefly noted:

FIG. 12 is an exploded view taken, in general, in a lateral to medial direction, of another embodiment of a glenoid component for a glenohumeral joint implant, which has a multi-point fixation glenoid component mounting shell.

FIG. 13 is a top view, in general, of the assembled glenoid component of FIG. 12.

FIG. 14 is a perspective view, taken generally in a lateral to medial direction, of the assembled glenoid component of FIG. 12.

FIG. 18 is a superior view of yet another humeral implant hereof, which shows, among other things, internal and external rotation capability of the implant.

FIG. 19 is a lateral view of the implant of FIG. 18, which shows, among other things, anterior and posterior rotation capability of the implant.

FIG. 20 is an anterior plan view of the implant of FIG. 18, as if implanted in a left human humerus, which also shows, among other things, abduction and adduction motion capability of the implant.

Figure 1:
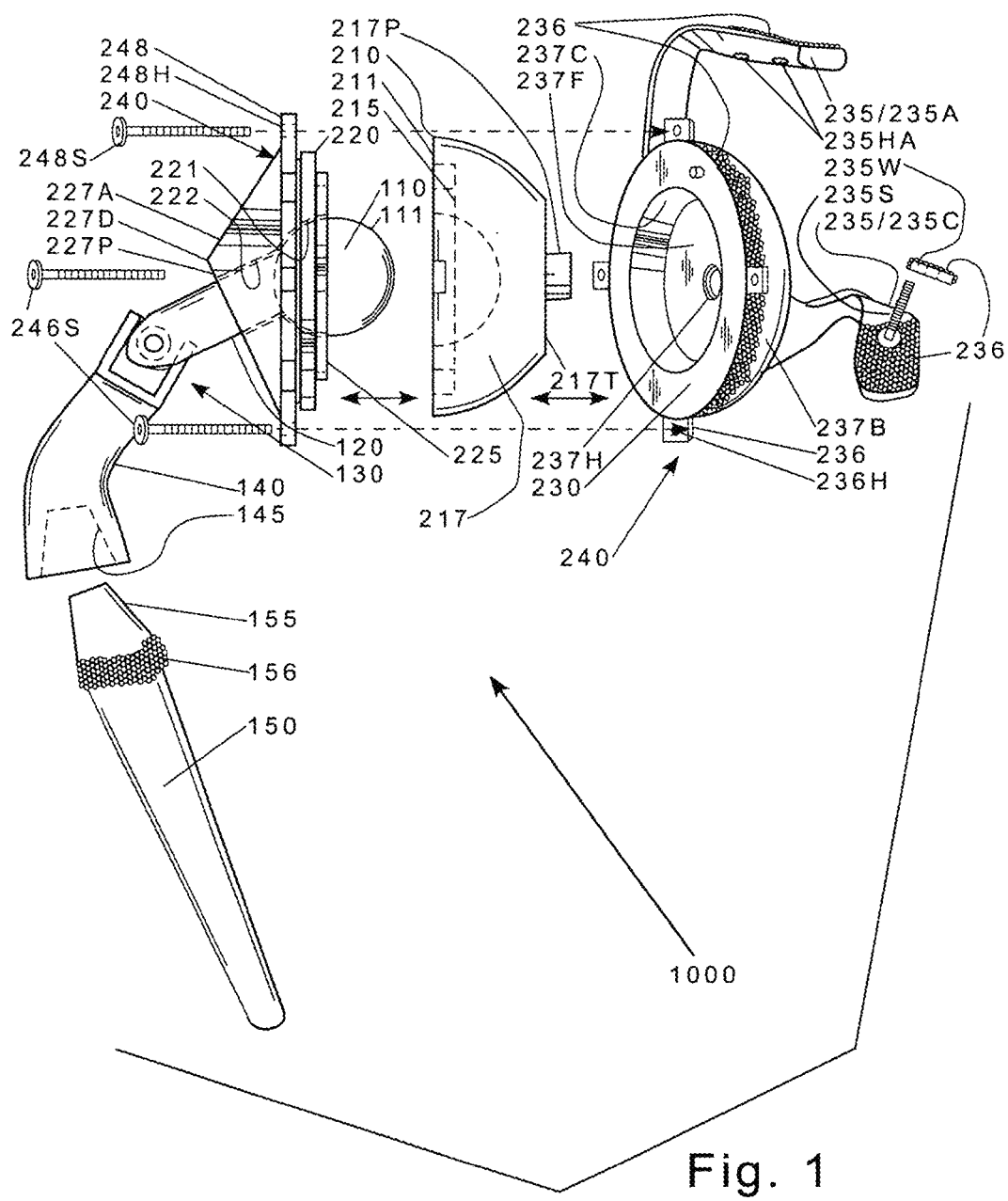
FIG. 1 is an exploded plan view of a shoulder joint implant ensemble hereof, depicted generally as a top view for a left shoulder or a bottom view for a right shoulder.
Figure 2:
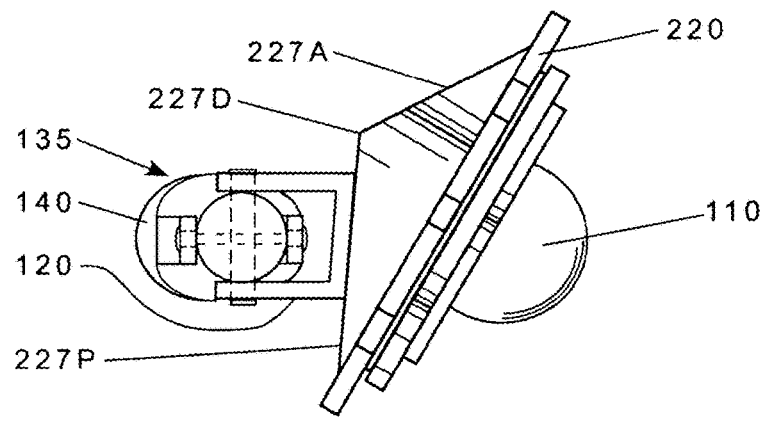
FIG. 2 is a plan view of a portion of a humeral component mounted in a closure portion of a glenoid component from the ensemble of FIG. 1.
Figure 3:
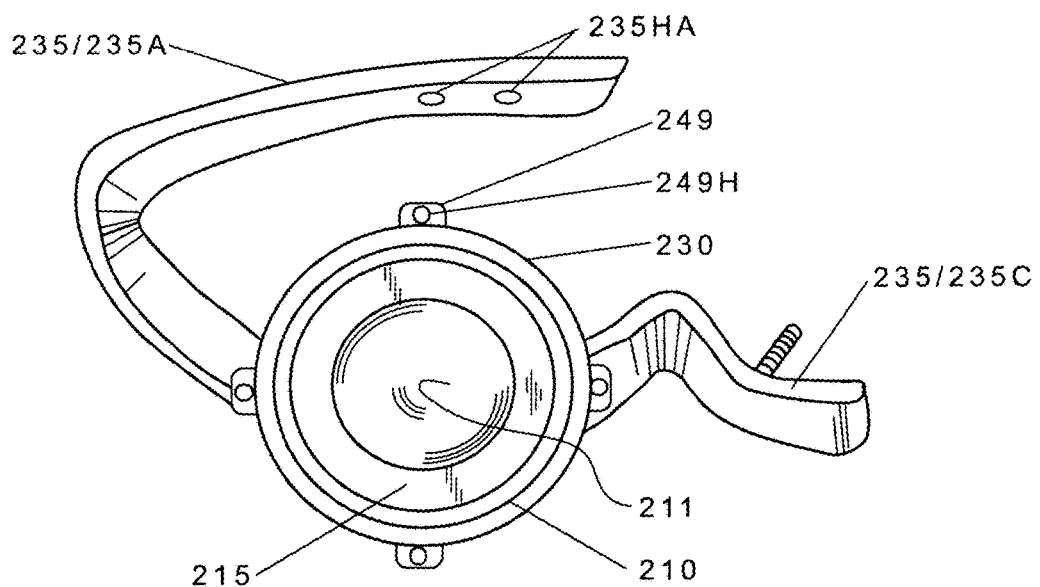
FIG. 3 is a lateral to medial view of part of a glenoid component, which has a multi-point fixation glenoid mounting shell with a plurality of mounting arms, from the ensemble of FIG. 1.
Figure 4:
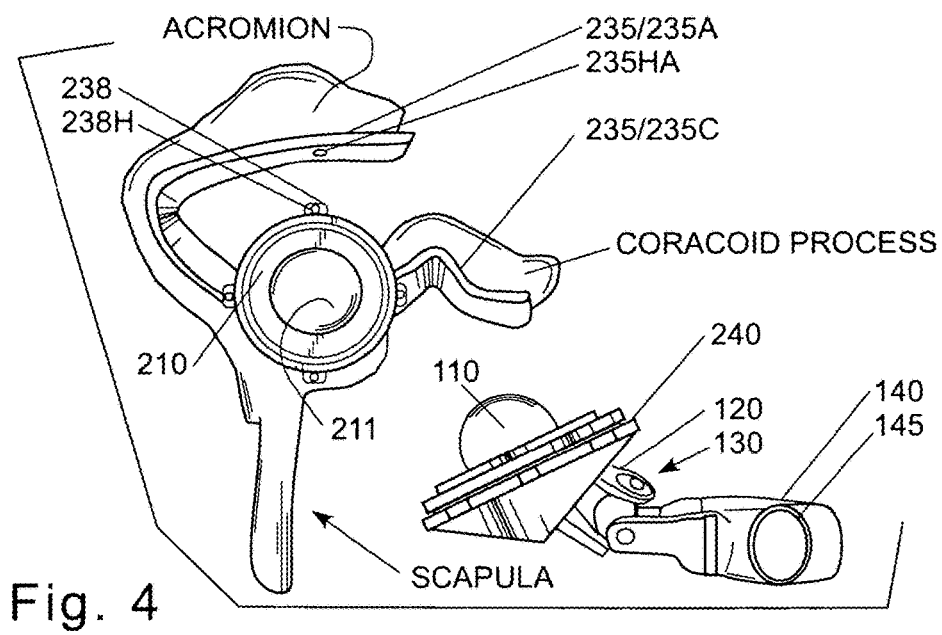
FIG. 4 is a lateral to medial view of part of the ensemble of FIG. 1, exploded, with part of its glenoid component also as in FIG. 3, mounted in a human right shoulder bone, the scapula with its acromion and coracoid process, through multi-point fixation.
Figure 5:
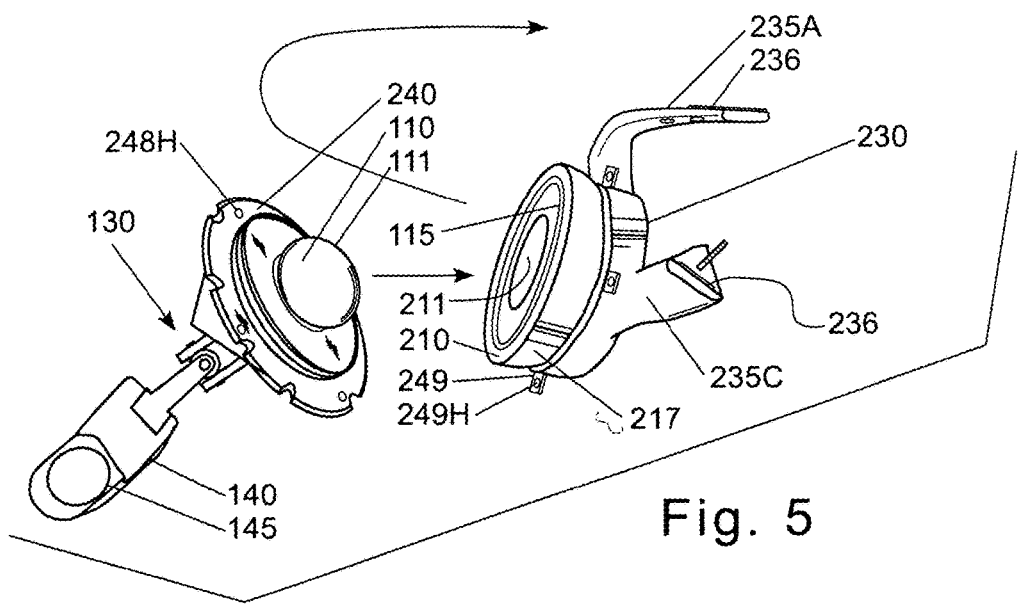
FIG. 5 is an exploded anterior to posterior view of the part ensemble of FIG. 4, in a position in general as if for mounting in the human right shoulder bone (not illustrated).
Figure 6:
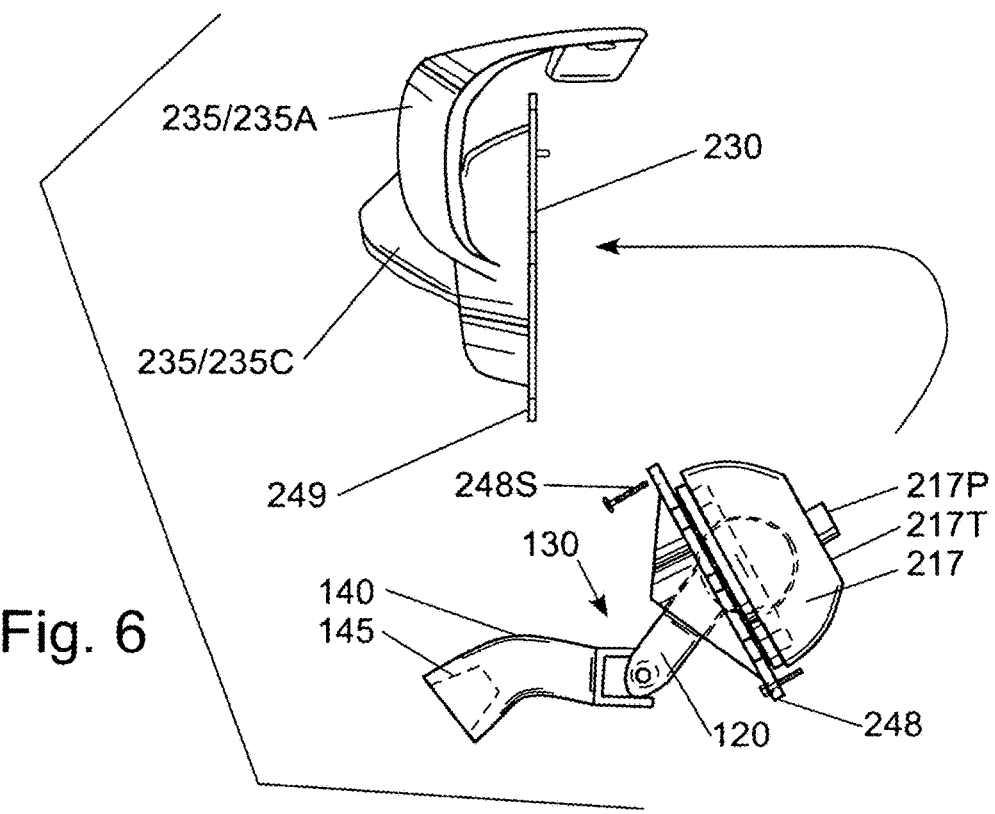
FIG. 6 is a posterior to anterior view of the multi-point fixation glenoid component mounting shell in the part ensemble of FIG. 4, again, in a position, in general, as if for mounting in the human right shoulder bone (not illustrated).
Figure 7:
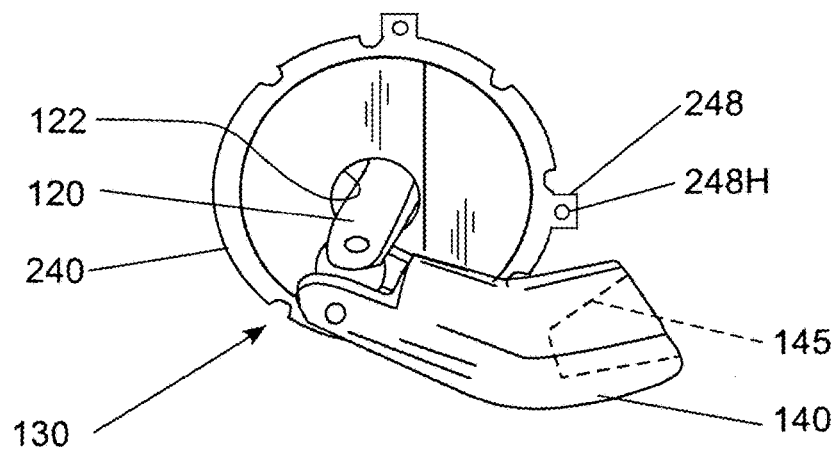
FIG. 7 is a perspective view of part of the ensemble of FIG. 1, without glenoid component mounting shell and humeral stem, looking in a lateral to medial direction and from a top position, as otherwise with its glenoid component mounted in the shoulder and the humeral component directed anteriorly.
Figure 8:
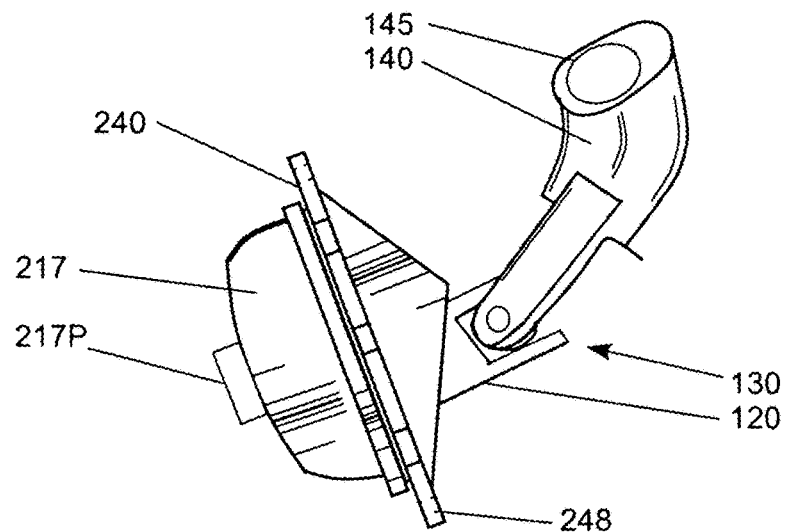
FIG. 8 is a top view of the part ensemble of FIG. 7, positioned as in FIG. 7.
Figure 9:
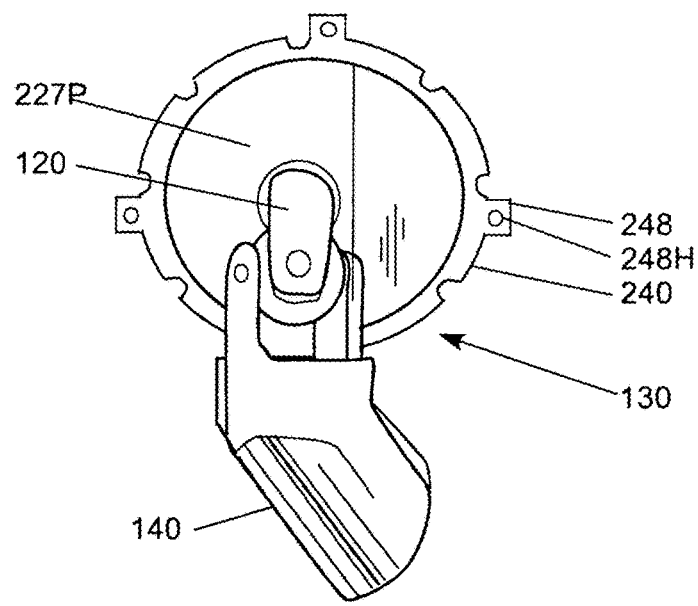
FIG. 9 is a view of the part ensemble of FIG. 7, but having its humeral component directed downwardly.
Figure 10:
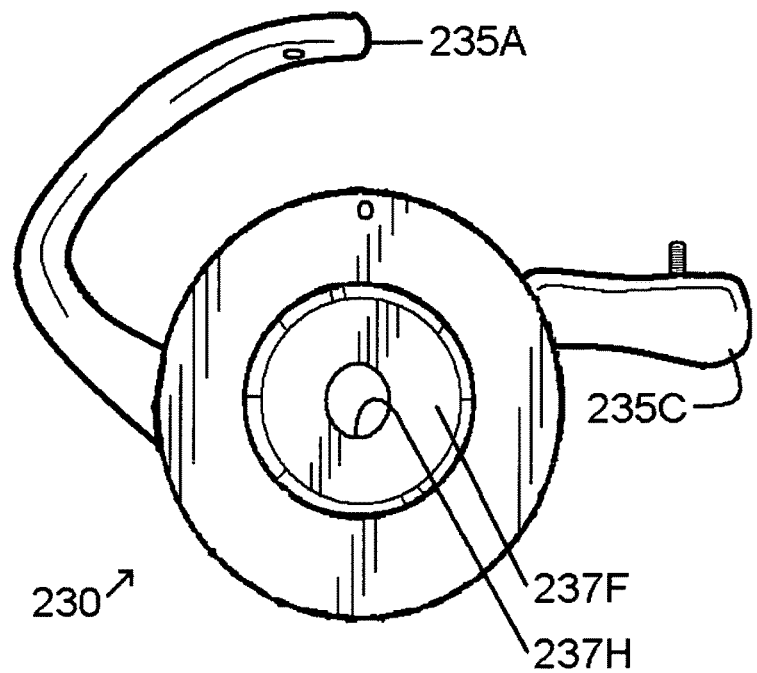
FIG. 10 is a lateral to medial view of a multi-point fixation glenoid component mounting shell. Compare, FIGS. 1 and 3-6.
Figure 11:
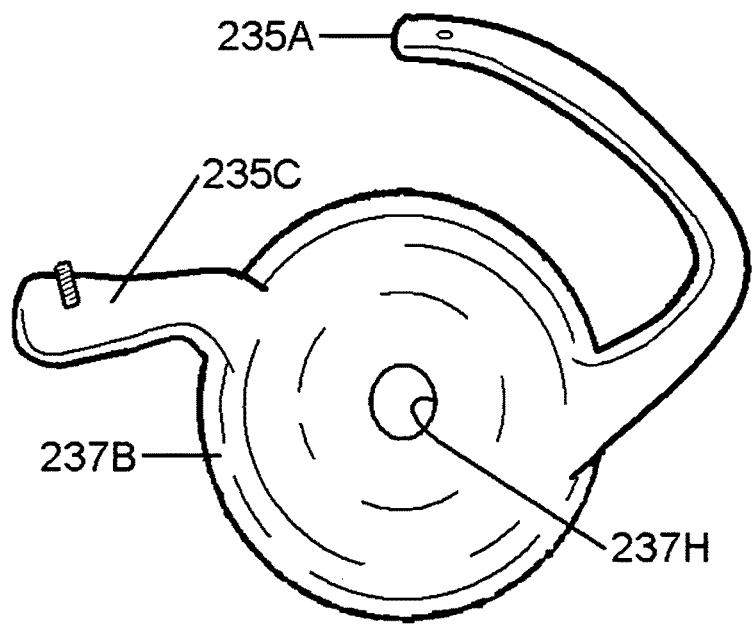
FIG. 11 is a medial to lateral view of the mounting shell of FIG. 10.

The present shoulder joint implant or implant component can be further understood by the detail set forth below, which may be read in view of the drawings. As with the foregoing disclosure, the following is to be taken in an illustrative and not necessarily limiting sense.

The present shoulder joint implant or implant component is for implantation as an ensemble for total glenohumeral joint arthroplasty, or at least as a glenoid or humeral component therefor. The implant may be considered to be a captured element shoulder joint implant. For example, the captured part coupling mechanism is provided in a total glenohumeral joint implant ensemble, with or without a glenoid component that is the multi-point fixation glenoid component—whereas the multi-point fixation glenoid component can be provided as a stand alone component in a total glenohumeral joint implant ensemble with the captured part coupling mechanism, which itself may or may not employ a humeral stem, or apart from the captured part coupling mechanism such as employed in conjunction with simple humeral head resurfacing or stemmed humeral head components; or may be employed as or in conjunction with an implant for revisional shoulder surgery to articulate against a previously implanted artificial humeral head implant and/ or even for initially performed surgery to articulate against a natural humeral head, which may be a form of arthroplasty. It may be configured to articulate against a previously implanted artificial humeral part implant such as, for example, a reverse shoulder humeral cup. The captured part coupling mechanism is especially useful in patients without viable rotator cuff structures. The multi-point fixation glenoid component can be embodied, for instance, with two- or three-point fixation, which employs fixation at two or three spaced-apart points, or areas, for example:

Glenoid area and acromial process (acromion), say, with the mount or shell for a glenoid cup insert, or a ball as in a reverse shoulder or other appropriately engineered configuration insert, to mount to the glenoid area of the scapular bone and an elongate mounting arm to mount to the acromion for two-point fixation;

Glenoid area and coracoid process (coracoid), say, with the mount or shell for a glenoid cup insert, or a ball as in a reverse shoulder or other appropriately engineered configuration insert, to mount to the glenoid area of the scapular bone and an elongate mounting arm to mount to the coracoid for two-point fixation; or Glenoid area and acromion plus coracoid, say, with the mount or shell for a glenoid cup insert, or a ball as in a reverse shoulder or other appropriately engineered configuration insert, to mount to the glenoid area of the scapular bone and a first elongate mounting arm to mount to the acromion plus a second elongate mounting arm to mount to the coracoid for three-point fixation.

The humeral implant or implant component with provision for restoration of the center of rotation as in a normal shoulder, can be configured for implantation in an ensemble for total glenohumeral joint arthroplasty, in which it may register with and articulate against an artificial glenoid cup implant component, or for implantation itself in glenohumeral joint hemiarthroplasty, in which it can register with and articulate against a natural glenoid. Either or both the humeral component or the glenoid component may include provision(s) for bio-ingrowth, may be made to be surgically cementable and through that be surgically cemented and/or be made to be attached to tissue, especially bone, with mechanical fastener attachment such as by bone screw(s), pin(s), staple(s), plate(s), strap(s) and/or suture(s). The glenohumeral joint can be that of a human being.

The implant and its components can be made of any suitable material(s). Biocompatible material(s) is(are) generally employed, which, for instance, may include a suitable metal such as Titanium or alloy thereof, for example, a Titanium-6Aluminum-4Vanadium extra low interstitial (Ti-6Al-4V ELI) alloy for surgical implant applications as specified by ASTM F 136-08 or the like, Cobalt or alloy thereof, for example, a Cobalt-28Chromium-6Molybdenum (Co—Cr) alloy as specified by ASTM F 75-07, ASTM F 799-09 or the like and/or a stainless steel as specified by ASTM F 138-08, ASTM F 621-08 or the like; a suitable ceramic such as an alumina or zirconia ceramic, for example, a magnesium oxide stabilized tetragonally toughened alumina (MgTTZ) as set forth in Pub. No. US 2006/0025866 A1 by Serafin, Jr. et al. and as may conform to ASTM F-2393-04; and/or a suitable composite or plastic such as a polyurethane or polyethylene, for example, an ultra high molecular weight polyethylene (UHMWPE) as specified by ASTM F 648-07 or ASTM F 2565-06. Known methods can be employed.

The implant and its components can be any suitable size. Custom sizes, which conform to specifics of a certain patient, and standard sizes, which conform to a general class and size of patient, may be provided. Mix and match modularity may be provided.

With reference to the drawings, the following is noted:

With respect to FIGS. 1-14, in general, the following is noted:

Shoulder joint implant ensemble 1000 includes humeral component 100 and glenoid component 200. The ensemble 1000 is adapted for surgical replacement of an adult human glenohumeral joint, and is a total joint implant.

The humeral component 100, for example, made with Co—Cr alloy, includes ball-like head 110 having smooth, hard articular surface 111, which is attachable through inner neck 120 to universal joint 130. Distally connected to the universal joint is outer neck 140, which can have receptacle 145, for example, in a form of a cup provided with a female Morse taper. For stem modularity, to the outer neck 140 with its receptacle 145 may be attached humeral stem 150 through mounting protrusion 155, for example, in a form of a trunnion provided as a truncated cone having a male Morse taper corresponding to the Morse taper of the noted cup form of the receptacle 145. Generally speaking, the humeral stem 150, which may have a portion or all of it coated with porous coating 156 for ingrowth of bone, is adapted for insertion in intramedullary bone stock of the upper humerus. The humeral stem 150 may be provided in a form that is one-piece with respect to the outer neck 140 without intervening receptacle 145 and mounting protrusion 155. A humeral stem such as the stem 150 may be absent, with the remainder of the humeral component adapted for mounting on appropriately prepared humeral bone, say, through holes, screws and/or glue such as methylmethacrylate surgical cement, or through provision of further mounting features in lieu of a stem such as the stem 150. In lieu of metal such as, for example, the Co—Cr alloy, the entire humeral component 100 or parts thereof may be made substantially of ceramic, for instance, MgTTZ.

The glenoid component 200, 200', for example, made with Ti-6Al-4V ELI alloy and UHMWPE, includes UHMWPE glenoid cup 210, 210', optionally having location notches 210N, but having concave articular surface 211, 211' upon which an opposing portion of the articulating surface 111 of the head 110 can articulate; closing feature 215 in the glenoid cup 210, which is a closable glenoid cup, such as in a form of an annular outer-facing groove, which may or may not carry screw threads, a bayonet protrusion receiving recess for bayonet attachment, or other attachment enhancing feature; back surface 217, which may have a protrusion 217P and/or truncated portion 217T; and optional range of motion cut away portion 219. The glenoid component 200 can include UHMWPE cup closure 220 having concave surface 221, which may be considered to be available for articulation against another opposing portion of the articulating surface 111 of the head 110, inner neck passing hole 222, complementary closing feature 225 such as in a form of an annular inner-facing protrusion, which may or may not carry screw threads, a bayonet projection for insertion into the bayonet protrusion receiving recess for bayonet attachment, or other attachment enhancing feature, and which mates in registry, screwing or bayonet attachment relationship, and so forth, with the closing feature 215, and outer surface 227, which can include anterior "cut-away" surface 227A, which may be in a planar configuration and provide for extended range of motion for the humeral component 100 anteriorly, dividing ridge 227D, which may be in a form of a peak, and posterior "cut-away" surface 227P, which also may be in a planar configuration and provide for extended range of motion for the humeral component 100 posteriorly. The glenoid component 200 with its closable cup 210 and cup closure 220 parts can envelope and surround the ball-like head 110 of the humeral component 100 when the humeral component 100 is mounted to the glenoid component 200, such that the humeral head 110 can articulate against the articular surface 111 of the glenoid cup 210 (and perhaps in some instances against the articular surface 221 of the cup closure 220) and such that the universal joint connection 130 is outside the glenoid component 200. To provide for this, in assembly, the inner neck 120 can be inserted through the inner neck passing hole 222 with travel of the head 110 able to be stopped by the surface 221; then the universal joint 130 can be assembled to provide the ensemble 1000 with or without the humeral stem 150. In lieu of plastic such as, for example, the UHMWPE, the cup 210 and cup closure 220 may be made substantially of metal or ceramic, say, MgTTZ. The glenoid component 200, however, may be of one piece in lieu of the two parts 210, 220 to surround the head 110, for instance, by molding such from plastic about the head 110 of a previously assembled humeral component 100. Otherwise, a humeral head, for example, the articular surface 111 of the ball 110, articulates against the surface 211' without capture by a glenoid component.

Further, a glenoid component for a glenohumeral joint implant, which can include the glenoid component 200, can include a body of a cup or mount 230, 230' for a cup such as the cup 210, 210' which mount 230, 230' for example, made of Ti-6Al-4V ELI, may be in a form of a shell with elongate mounting arms 235, 235' to mount to shoulder bone, for instance, with one arm 235A, 235A' for mounting to the acromion, which may be a longer bent arm as the arm 235A adapted in form to be mounted to the acromion through screw(s) passed through hole(s) 235HA, and another arm 235C, 235C' for mounting to the coracoid process, which may be a shorter bent arm as the arm 235C adapted in form to be mounted to the coracoid process through screw(s) passed through hole(s) 235HC. Thus, multi-point fixation, here, for example, three-point fixation, is provided, which significantly enhances stability of the component when implanted. Spacer(s), say, in a form of washer(s) 235W, may be employed to assist in positioning. Surgical cement may be employed also. Porous coating 236 for ingrowth of bone may be provided. The mount 230 can also include back 237B and cup-receiving concave surface 237C, which may include flat surface 237F to register with the truncated portion 217T and/or one or more other features such as to secure a cup such as the cup 210 through its rear 217 that may include hole(s) such as the centered hole 237H to accept protrusion(s) on the back of the cup 210 such as the protrusion 217P, or to thread screws therethrough or receive glue such as surgical cement therein and into or onto the cup 210. The hole 237H can have a lateral direction facing countersink to provide a lip or ledge along the back 237B to hold such glue. Shell cut away 239 may be provided so as to accommodate the cut away 219.

The cup closure 220 and cup or mount 230 for the cup 210 may be secured together even further by auxiliary closing aid(s) 240. For instance, the cup closure 220 may have an auxiliary closing aid component 240 in a form of a radially extending ridge or protruding portion or flange 248 that has a hole 248H through which screw 248S may be passed. The glenoid mount 230 can have protruding portion or flange 239 that has a hole 249H, which may be threaded and through which the screw 248S passes possibly with threading therein. Glue such as surgical cement may be used as an auxiliary closing aid or in conjunction with the auxiliary closing aid(s) 240.

Figure 15:
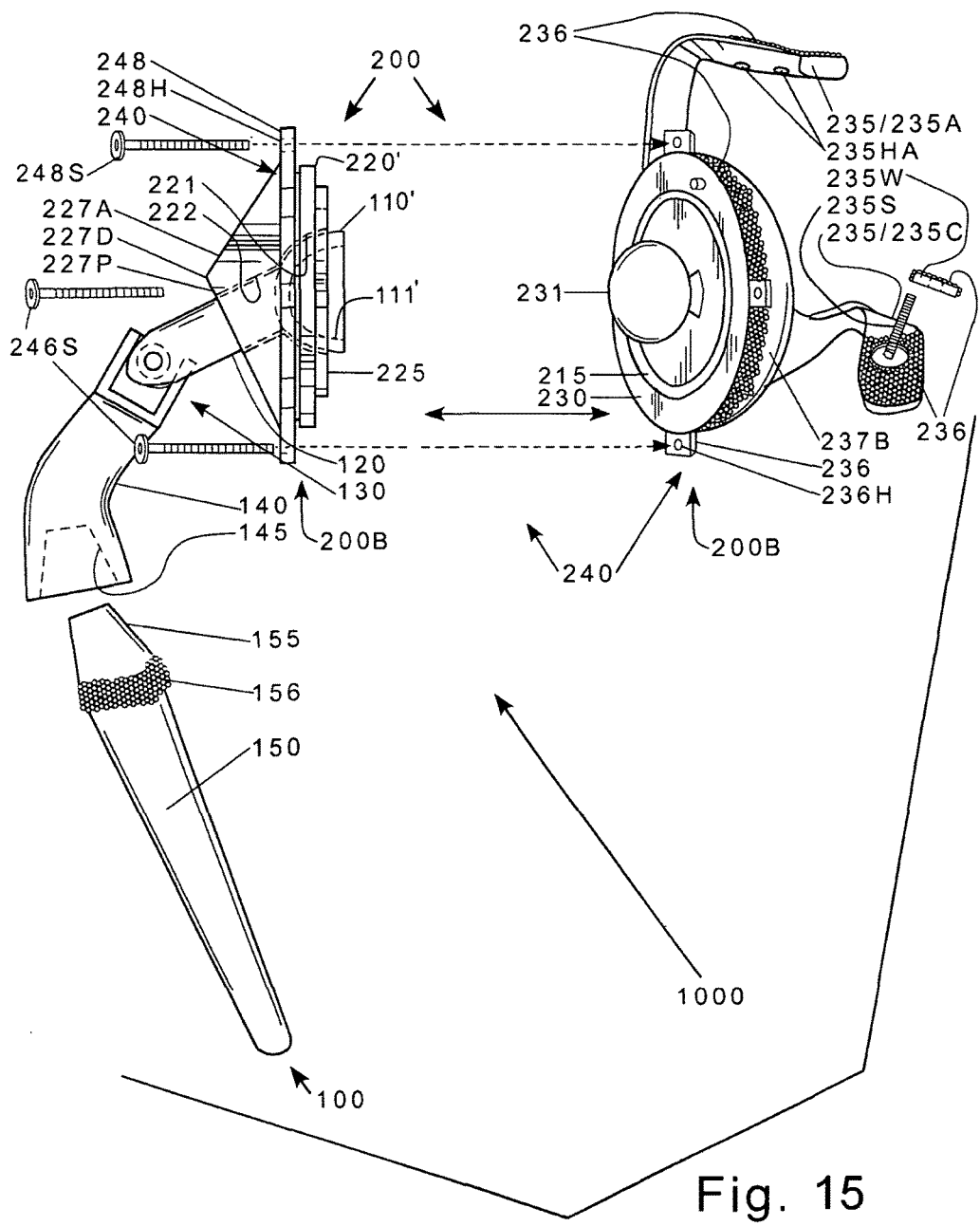
FIG. 15 is an exploded plan view of a reverse shoulder joint implant ensemble hereof, depicted generally as a top view for a left shoulder or a bottom view for a right shoulder.
Figure 16:
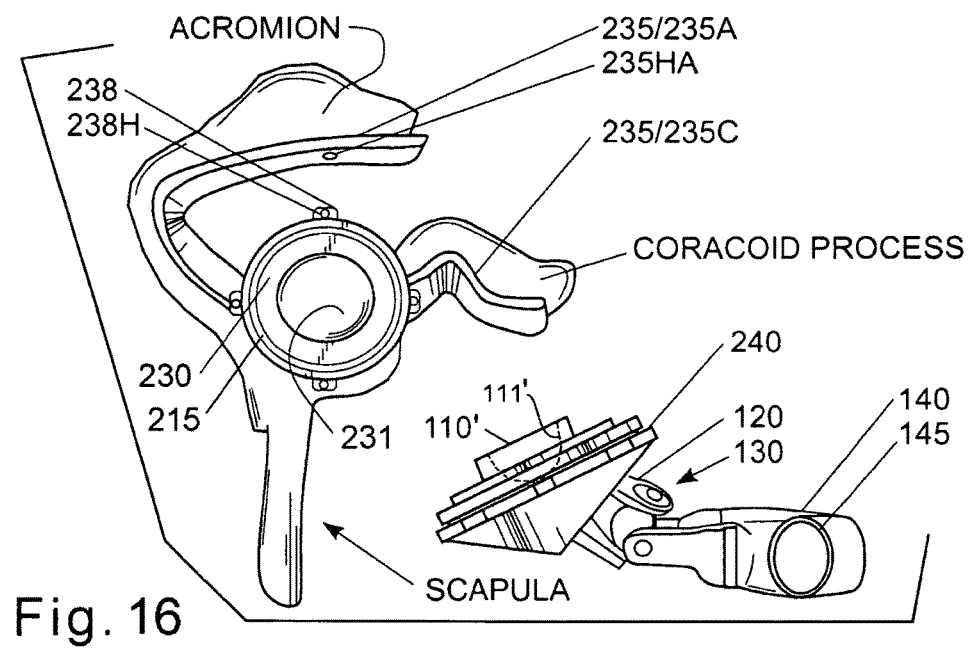
FIG. 16 is a lateral to medial plan view of part of the ensemble of FIG. 15, exploded, with part of its glenoid component mounted in a human right shoulder bone, the scapula with its acromion and coracoid process, through multi-point fixation.
Figure 17:
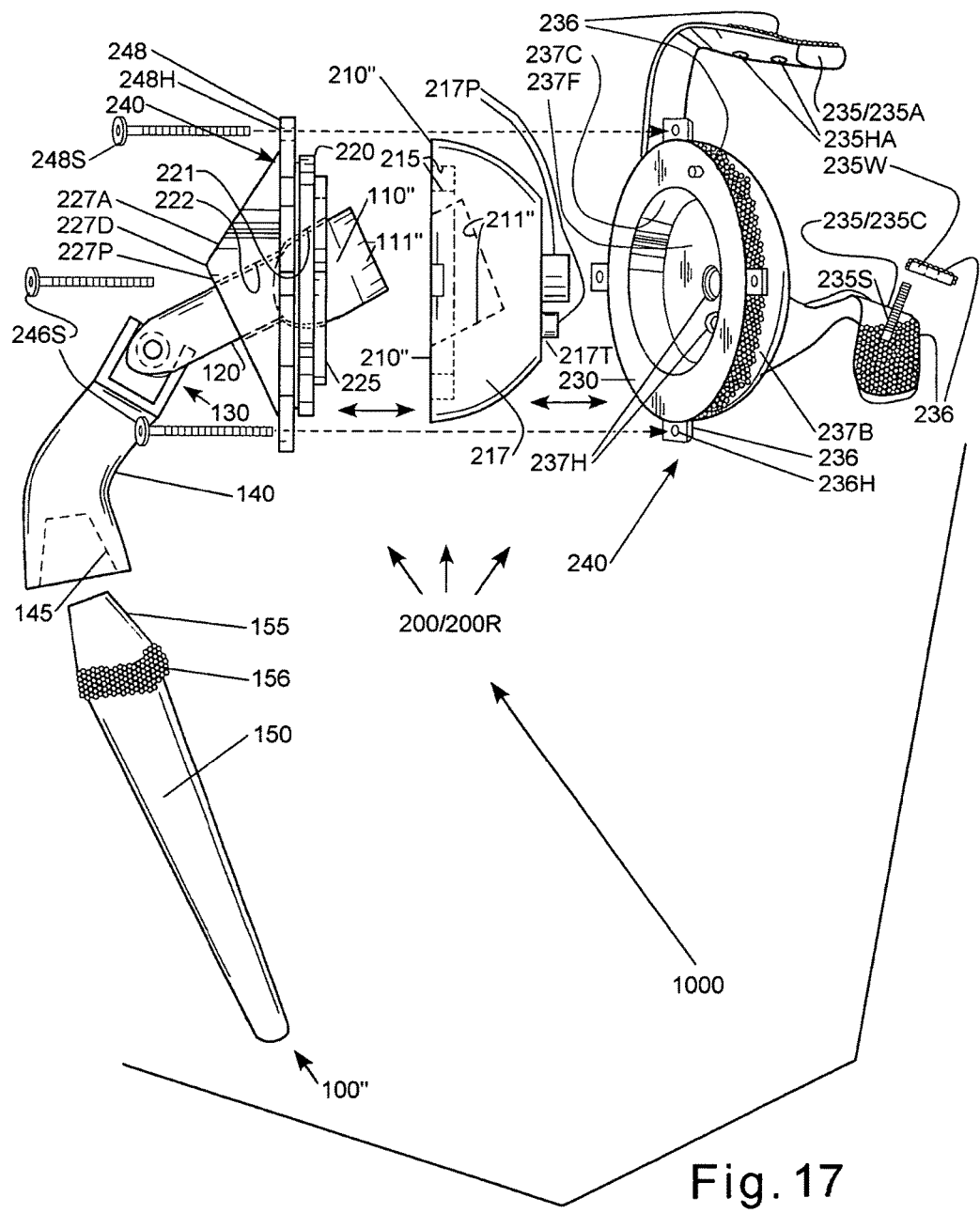
FIG. 17 is an exploded view of another shoulder joint implant ensemble hereof, having barrel- or disc-like humeral head to recessed glenoid articulation, depicted generally as a top view for a left shoulder or a bottom view for a right shoulder.

With respect to FIGS. 15-17, in general, the following is noted:

Shoulder joint implant ensemble 1000 includes humeral component 100 and glenoid component 200. The ensemble 1000 is adapted for surgical replacement of an adult human glenohumeral joint, and is a total joint implant.

The humeral component 100, for example, made with Co—Cr alloy, may include a cup-like head 110' having smooth, hard articular concave surface 111' or a barrel- or disc-like head 110" having smooth, hard articular surfaces 111", which in each case is attachable through inner neck 120 to universal joint 130. Distally connected to the universal joint is outer neck 140, which can have receptacle 145, for example, in a form of a cup provided with a female Morse taper. For stem modularity, to the outer neck 140 with its receptacle 145 may be attached humeral stem 150 through mounting protrusion 155, for example, in a form of a trunnion provided as a truncated cone having a male Morse taper corresponding to the Morse taper of the noted cup form of the receptacle 145. Generally speaking, the humeral stem 150, which may have a portion or all of it coated with porous coating 156 for ingrowth of bone, is adapted for insertion in intramedullary bone stock of the upper humerus. The humeral stem 150 may be provided in a form that is one-piece with respect to the outer neck 140 without intervening receptacle 145 and mounting protrusion 155. A humeral stem such as the stem 150 may be absent, with the remainder of the humeral component adapted for mounting on appropriately prepared humeral bone, say, through holes, screws and/or glue such as methylmethacrylate surgical cement, or through provision of further mounting features in lieu of a stem such as the stem 150. In lieu of metal such as, for example, the Co—Cr alloy, the entire humeral component 100 or parts thereof may be made substantially of ceramic, for instance, MgTTZ.

The glenoid component 200, as appropriate, may be provided, for example, in ball form 200B or recess form 200R. The ball form 200B would be employed in a reverse shoulder configuration with the cup head 110' or other corresponding cup head that may not be constrained, and the recess form 200R would be employed with the barrel- or disc-like head 110" or other corresponding cup head that may not be constrained.

The glenoid component 200B, for example, made with Co—Cr alloy and optionally with a portion of UHMWPE, has Co—Cr body 230 with articulating ball 231. The ball 231 articulates against head cup 111". The glenoid component 200B can include Co—Cr or UHMWPE closure 220' having concave surface 221, which may be considered to be available for articulation against a laterally disposed portion of the articulating surface 111' of the head 110', inner neck passing hole 222, closing feature 215, which assists in securing the closure 220' to a corresponding groove 235 in the body 230; and outer surface 227, which can include anterior "cut-away" surface 227A, which may be in a planar configuration and provide for extended range of motion for the humeral component 100' anteriorly, dividing ridge 227D, which may be in a form of a peak, and posterior "cut-away" surface 227P, which also may be in a planar configuration and provide for extended range of motion for the humeral component 100' posteriorly. The glenoid component 200 with its closure 220' can envelope and surround the cup-like head 110' of the humeral component 100 when it is mounted to the glenoid component 200B, such that the humeral cup 110' can articulate against the glenoid ball 231 (and perhaps in some instances against the articular surface 221 of the cup closure 220) and such that the universal joint connection 130 is outside the glenoid component 200. To provide for this, in assembly, the inner neck 120 can be inserted through the inner neck passing hole 222 with travel of the head 110 able to be stopped by the surface 221; then the universal joint 130 can be assembled to provide the ensemble 1000 with or without the humeral stem 150. In lieu of metal, ceramic, say, MgTTZ may be employed. Otherwise, a humeral cup head, for example, the articular surface 111' of the cup head 110', articulates against the surface 231 without capture by a glenoid component.

The glenoid component 200R, for example, made with Ti-6Al-4V ELI alloy and UHMWPE, may include glenoid insert 210", say, of UHMWPE, optionally having location notches 210N, but having an articular surface 211" upon which an opposing portion of the articulating surface 111" of the barrel- or disc-like head 110" can articulate; closing feature 215 in the glenoid cup 210", which is a closable glenoid cup, such as in a form of an annular outer-facing groove, which may or may not carry screw threads, a bayonet protrusion receiving recess for bayonet attachment, or other attachment enhancing feature; and back surface 217, which may have a protrusion 217P and/or truncated portion 217T. Optionally, a range of motion cut away portion may be provided. The glenoid component 200R can include UHMWPE cup closure 220 having cup surface 221, which may be considered to be available for articulation against a generally laterally directed portion of the head 110", inner neck passing hole 222, complementary closing feature 225 such as in a form of an annular inner-facing protrusion, which may or may not carry screw threads, a bayonet projection for insertion into the bayonet protrusion receiving recess for bayonet attachment, or other attachment enhancing feature, and which mates in registry, screwing or bayonet attachment relationship, and so forth, with the closing feature 215, and outer surface 227, which can include anterior "cut-away" surface 227A, which may be in a planar configuration and provide for extended range of motion for the humeral component 100 anteriorly, dividing ridge 227D, which may be in a form of a peak, and posterior "cut-away" surface 227P, which also may be in a planar configuration and provide for extended range of motion for the humeral component 100 posteriorly. The glenoid component 200R with its closable cup 210 and cup closure 220 parts can envelope and surround the head 110" of the humeral component 100 when the humeral component 100 is mounted to the glenoid component 200R, such that the humeral head 110" can articulate against the articular surface 211" of the glenoid cup 210" (and perhaps in some instances against the articular surface 221 of the cup closure 220) and such that the universal joint connection 130 is outside the glenoid component 200. To provide for this, in assembly, generally as above, the inner neck 120 can be inserted through the inner neck passing hole 222 with travel of the head 110" able to be stopped by the surface 221; then the universal joint 130 can be assembled to provide the ensemble 1000 with or without the humeral stem 150. In lieu of plastic such as, for example, the UHMWPE, the cup 210" and cup closure 220 may be made substantially of metal or ceramic, say, MgTTZ. The glenoid component 200R, however, may be of one piece in lieu of the two parts 210", 220 to surround the head 110", for instance, by molding such from plastic about the head 110" of a previously assembled humeral component 100. Otherwise, a humeral head, for example, the articular surface 111" of the head 110", articulates against the surface 211' without capture by a glenoid component.

Further, a glenoid component for a glenohumeral joint implant, which can include the glenoid components 200B and 200R, can include a body or mount 230 for a part such as the cup 210" which mount 230, for example, made of Ti-6Al-4V ELI, may be in a form of a shell with elongate mounting arms 235 to mount to shoulder bone, for instance, with one arm 235A for mounting to the acromion, which may be a longer bent arm adapted in form to be mounted to the acromion through screw(s) passed through hole(s) 235HA, and another arm 235C for mounting to the coracoid process, which may be a shorter bent arm adapted in form to be mounted to the coracoid process through screw(s) passed through hole(s) 235HC. Thus, multi-point fixation, here, for example, three-point fixation, is provided, which significantly enhances stability of the component when implanted. Spacer(s), say, in a form of washer(s) 235W, may be employed to assist in positioning. Surgical cement may be employed also. Porous coating 236 for ingrowth of bone may be provided. The mount 230 can also include back 237B and cup-receiving concave surface 237C, which may include flat surface 237F to register with the truncated portion 217T and/or one or more other features such as to secure a cup such as the cup 210" through its rear 217 that may include hole(s) such as the centered and/or offset holes 237H to accept protrusion(s) on the back of the cup 210" such as the protrusion 217P, or to thread screws therethrough or receive glue such as surgical cement therein and into or onto the cup 210. The hole(s) 237H can have a lateral direction facing countersink to provide a lip or ledge along the back 237B to hold such glue. Shell cut away 239 may be provided so as to accommodate the cut away 219.

The cup closure 220 and cup or mount 230 for the cup 210 may be secured together even further by auxiliary closing aid(s) 240. For instance, the cup closure 220 may have an auxiliary closing aid component 240 in a form of a radially extending ridge or protruding portion or flange 248 that has a hole 248H through which screw 248S may be passed. The glenoid mount 230 can have protruding portion or flange 239 that has a hole 249H, which may be threaded and through which the screw 248S passes possibly with threading therein. Glue such as surgical cement may be used as an auxiliary closing aid or in conjunction with the auxiliary closing aid(s) 240.

With respect to FIGS. 18-20, in general, the following is noted:

Humeral implant 100 for the glenohumeral joint, which would include glenoid socket area 8 and humerus 9, includes glenoid interacting portion 10, humeral interacting portion 20, and universal joint 30. The humeral implant 100 is adapted for surgical implantation in an adult human glenohumeral joint.

The humeral component 100, which, for instance, generally may be made with Co—Cr alloy throughout except where noted, includes the glenoid interacting portion 10, which has glenoid facing neck 11 and securement plate 12 embedded in UHMWPE head 13 or otherwise positioned in cavity 14 within the head 13. The head 13 has radial, deep facing surface 15 for registering with and articulating against an artificial, implanted glenoid cup or natural glenoid tissue. The humeral interacting portion 20 has humeral intramedullary stem 21, stabilizing fins 22, and stem riser 23. The glenoid facing neck 11 and stem riser 23 connect with the universal joint 30.

Surgical implantation of the present humeral implant, which would include the humeral implant 100, in general, can be carried out by methods known to one skilled in the art of orthopedic surgery.

CONCLUSION TO THE INVENTION

The present invention is thus provided. Various feature(s), part(s), step(s), subcombination(s) and/or combination(s)

may be employed with or without reference to other feature(s), part(s), step(s), subcombination(s) and/or combination(s) in the practice of the invention, and numerous adaptations and modifications can be effected within its spirit, the literal claim scope of which is particularly pointed out as follows:

I claim:

1. A device comprising a shoulder joint implant with, or implant component for, a captured ball coupling mechanism including at least one of an artificial humeral component and an artificial glenoid component, which is useful in or as an ensemble for total joint replacement of a glenohumeral joint, wherein one and only one of the following sets of additional features (A or B) is also present therewith:

(A) the humeral component includes a ball-like head attachable to a universal joint connection; and the glenoid component includes a closable glenoid cup having a concave articular surface, which glenoid component can envelope and surround the ball-like head of the humeral component when the humeral component is mounted to the glenoid component, such that the head can articulate against the articular surface of the glenoid cup and such that the universal joint connection is outside the glenoid component, wherein the universal joint connection has a yoke, is connectable to a mount for mounting to or in a humeral bone, and allows the mount and the ball-like head limited freedom of movement in any direction while transmitting rotary motion between the mount and the ball-like head;

(B) the humeral component includes an articulatable part attachable to a universal joint connection; and the glenoid component includes a closable glenoid part having a corresponding articular surface to that of the articulatable part, which glenoid component can envelope and surround the articulatable part of the humeral component when the humeral component is mounted to the glenoid component, such that the articulatable part can articulate against the corresponding articular surface of the glenoid part and such that the universal joint connection is outside the glenoid component, wherein the universal joint connection has a yoke, is connectable to a mount for mounting to or in a humeral bone, and allows the mount and the articulatable part limited freedom of movement in any direction while transmitting rotary motion between the mount and the articulatable part.

2. The device of claim 1, wherein the set "B" is configured as a general type of reverse shoulder having a glenoid ball articulatable part.

3. The device of claim 1, which has the set "A."

4. The device of claim 1, which has the set "B."

5. The device of claim 2, which has the set "B."

6. The device of claim 1, further comprising a corresponding glenoid component, which provides for multi-point fixation and includes at least one elongate mounting arm for attaching to spaced-apart portion(s) of scapular bone.

7. The device of claim 6, wherein one and only one of the following sets of additional features (A' or B') is present therewith:

(A') the glenoid component includes a body of a cup, or a mount for a glenoid cup to be held with the mount, wherein the spaced-apart portion(s) of scapular bone include at least one of coracoid and acromion;

(B') the glenoid component includes a body of an articulatable part, or a mount for an articulatable glenoid part to be held with the mount, wherein the spaced-apart portion(s) of scapular bone include at least one of coracoid and acromion.

8. The device of claim 7, wherein the set "B" is configured as a general type of reverse shoulder having a glenoid ball articulatable part.

9. The device of claim 7, which has the sets "A" and "A'."

10. The device of claim 7, which has the sets "B" and "B'."

11. The device of claim 8, which has the sets "B" and "B'."

12. A shoulder joint implant or implant component for the glenohumeral joint, which comprises an artificial humeral component, which is useful in or as an ensemble for total joint replacement arthroplasty of a glenohumeral joint or which is useful in hemiarthroplasty in a glenohumeral joint where the artificial humeral component articulates against a natural glenoid, wherein:

the humeral component includes a radial head configured for registering against an artificial glenoid cup or natural glenoid tissue, and articulating against the same upon surgical implantation, which humeral component is attachable to a universal joint connection, wherein the universal joint connection has a yoke, is connectable to a mount for mounting to or in a humeral bone, allows the mount and the radial head limited freedom of movement in any direction while transmitting rotary motion between the mount and the radial head, and can provide for a center of movement; and the center of movement is generally within a volume defined by an upper head of a normal humerus, which otherwise would be resected and absent when the humeral component is implanted, and generally centered therein.

13. The implant or implant component of claim 12, wherein the humeral component includes a glenoid interacting portion, which has a glenoid facing neck and a securement plate embedded in a head or otherwise is positioned in a cavity within the head, wherein:

the head has a radial, deep facing surface for registering with and articulating against an artificial, implanted glenoid cup or natural glenoid tissue;

the humeral component has a humeral intramedullary stem and a stem riser; and the glenoid facing neck and the stem riser connect with the universal joint connection.

14. The implant or implant component of claim 12, wherein an artificial corresponding glenoid component is present to make for a total joint replacement implant ensemble useful for the aforementioned total joint replacement arthroplasty.

15. The implant or implant component of claim 14, wherein the artificial corresponding glenoid component embraces a body of a cup, or a mount for a glenoid cup to be held with the mount, and provides for multi-point fixation and includes two elongate mounting arms configured for attaching to spaced-apart portion(s) of scapular bone, which includes coracoid and acromion, wherein:

the elongate mounting arm includes a first bent arm configured to mount to the coracoid, and a second bent arm configured to mount to the acromion; and the first bent arm is shorter than the second bent arm.

* * * * *